(12) United States Patent
Mccaffrey et al.

(10) Patent No.: US 12,721,946 B2
(45) Date of Patent: Sep. 1, 2026

(54) PLEATED EXPANDABLE RESERVOIR FOR A WEARABLE DRUG DELIVERY DEVICE

(71) Applicant: INSULET CORPORATION, Acton, MA (US)

(72) Inventors: Maureen Mccaffrey, Arlington, MA (US); Daniel Allis, Boxford, MA (US)

(73) Assignee: INSULET CORPORATION, Acton, MA (US)

( * ) Notice: Subject to any disclaimer, the term of this patent is extended or adjusted under 35 U.S.C. 154(b) by 705 days.

(21) Appl. No.: 18/149,996

(22) Filed: Jan. 4, 2023

(65) Prior Publication Data

US 2023/0211077 A1 Jul. 6, 2023

Related U.S. Application Data

(60) Provisional application No. 63/296,619, filed on Jan. 5, 2022.

(51) Int. Cl.
*A61M 5/148* (2006.01)
*G16H 20/17* (2018.01)

(52) U.S. Cl.
CPC ............ *A61M 5/148* (2013.01); *G16H 20/17* (2018.01)

(58) Field of Classification Search
None
See application file for complete search history.

(56) References Cited

U.S. PATENT DOCUMENTS 4,276,170 A * 6/1981 Vaillancourt ........ B01D 36/001 96/6
4,991,743 A 2/1991 Walker
5,368,570 A 11/1994 Thompson et al.
5,906,592 A 5/1999 Kriesel et al.
6,146,362 A * 11/2000 Turnbull ............ A61M 39/045 604/905
6,740,059 B2 5/2004 Flaherty
7,137,964 B2 11/2006 Flaherty
7,303,549 B2 12/2007 Flaherty
(Continued)

FOREIGN PATENT DOCUMENTS

CN 107096091 A 8/2017
EP 0789146 A1 8/1997
(Continued)

OTHER PUBLICATIONS

European Search Report and Written Opinion, Application No. EP02768908, dated Apr. 30, 2010.
(Continued)

*Primary Examiner* — Manuel A Mendez
(74) *Attorney, Agent, or Firm* — Goodwin Procter LLP

(57) ABSTRACT

Disclosed herein are various embodiments providing an expandable, flexible reservoir for use in a wearable drug delivery device. The reservoir comprises a flexible enclosure made with plastic film which incorporates pleats forming the side walls thereof to increase the volume efficiency and to avoid a “pillowing” effect when the reservoir is filled. The pleats may be formed at non-right angles with respect to each other such as to form a curved side walls for the reservoir. In variations of the invention, various methods are disclosed for maintaining a vacuum with the reservoir during its shelf life.

18 Claims, 5 Drawing Sheets

(56) References Cited

U.S. PATENT DOCUMENTS

| | | | | |
|---|---|---|---|---|
| 8,632,504 | B2 * | 1/2014 | Young | A61M 5/2033 604/200 |
| 8,734,396 | B2 | 5/2014 | Wyss | |
| 11,246,802 | B2 * | 2/2022 | Tsakas | B65D 51/002 |
| 2003/0198558 | A1 | 10/2003 | Nason et al. | |
| 2004/0115068 | A1 | 6/2004 | Hansen et al. | |
| 2007/0255260 | A1 | 11/2007 | Haase | |
| 2007/0272705 | A1 * | 11/2007 | Beine | A61J 1/05 222/105 |
| 2008/0097318 | A1 * | 4/2008 | Adams | A61M 5/14228 604/131 |
| 2011/0108158 | A1 | 5/2011 | Huwiler et al. | |
| 2011/0319814 | A1 | 12/2011 | Sullivan et al. | |
| 2012/0241465 | A1 * | 9/2012 | Genosar | B65D 35/38 222/105 |
| 2017/0290975 | A1 | 10/2017 | Barmaimon et al. | |

FOREIGN PATENT DOCUMENTS

| | | | |
|---|---|---|---|
| EP | 1065378 | A2 | 1/2001 |
| EP | 2229970 | A1 | 9/2010 |
| EP | 2556815 | A1 | 2/2013 |
| WO | 2012065780 | A2 | 5/2012 |
| WO | 2013149186 | A1 | 10/2013 |

OTHER PUBLICATIONS

International Search Report and Written Opinion, Application No. PCT/US2019/042233, mailed Jan. 3, 2020, 14 pages.
International Search Report and Written Opinion, Application No. PCT/US2021/060148, mailed Mar. 17, 2022, 17 pages.
International Search Report and Written Opinion, Application No. PCT/US2022/016713, mailed Aug. 5, 2022, 19 pages.

* cited by examiner

PLEATED EXPANDABLE RESERVOIR FOR A WEARABLE DRUG DELIVERY DEVICE

RELATED APPLICATIONS

This application claims the benefit of U.S. Provisional Patent Application No. 63/296,619, filed Jan. 5, 2022, the contents of which are incorporated herein by reference in their entirety.

BACKGROUND

Many conventional drug delivery systems, in particular, systems which include a wearable drug delivery device, include a drug container within the wearable drug delivery device, often referred to as a reservoir, that stores a liquid drug for delivery to a user via a patient interface in accordance with an algorithm.

Such devices require a pump mechanism to move the liquid drug from the reservoir to the patient interface. The pump mechanism may be controlled by a microcontroller running software embodying an algorithm for determining an appropriate quantity of the liquid drug to dispense and to provide the proper signals to the pump mechanism to deliver the appropriate or desired quantity.

In certain prior art devices, the pump mechanism and the reservoir may be integrated. The reservoir and may be a rigid structure having a plunger disposed therein which pushes the liquid drug from the reservoir to the patient interface. The plunger may be driven by any known means, for example, via a motor-driven leadscrew or other well-known mechanisms.

In other prior art devices, the pump may be a separate structure from the reservoir. The pump typically comprises a chamber having a driven plunger disposed therein which, when driven in one direction, causes a suction which draws the liquid drug from the reservoir into the pump chamber and, when driven in the opposite direction, provides a pressure within the pump chamber that pushes the liquid drug from the pump chamber to the patient interface.

There are several problems with a reservoir configured as a rigid structure. First, the reservoir must have a large cross-sectional area that allows a plunger to be driven therethrough. As such, the reservoir is space inefficient because it precludes shaping the reservoir to fit the interior contours of the wearable drug delivery device, which may lead to wasted space. Second, the rigid reservoir, at least in an embodiment of the wearable drug delivery device having a separate pump mechanism from the reservoir, must have an air vent which allows air to be drawn into the reservoir as the liquid drug is drawn out of the reservoir by the pump mechanism, to avoid a creating a suction in the reservoir which would preclude being able to draw the liquid drug from the reservoir.

Therefore, it would be desirable to provide an improved design of a reservoir for a wearable drug delivery device that addresses at least some of the problems identified above.

SUMMARY OF THE INVENTION

The embodiments of the invention described herein provide a design for an expandable, flexible reservoir for use in a wearable drug delivery device. In a first embodiment of the invention, the reservoir comprises a flexible structure made with plastic film which incorporates pleats on the side walls thereof to increase the volume efficiency and to avoid a "pillowing" effect when the reservoir is filled. In a separate aspect of the first embodiment, the flexible structure may be made of a shape designed to fit the interior contours of one or more housings of the wearable drug delivery device by incorporating pleats which are not at right angles with respect to each other such as to form curved side walls.

Any flexible film reservoir has a risk of air residing in the reservoir. Air in the reservoir poses a risk because, if it gets into the pump mechanism, it could hinder pump function and could lead to under-delivery of the liquid drug to the patient. During the manufacturing process, the reservoir may be evacuated of air and vacuum sealed to prevent air from entering the reservoir during the shelf life of the device. However, in most instances, the fluid port of the reservoir represents a weak link in maintaining the vacuum within the reservoir, and air may find its way into the reservoir during the shelf life of the device.

Therefore, in a second embodiment of the invention, the pleated flexible film reservoir is evacuated of air during the manufacturing process and fitted with a hermetic seal which seals the fluid port from the interior of the reservoir. The hermetic seal may be designed to be mechanically weak, such that pressure from the liquid drug being forced from the fluid port into the reservoir breaks the hermetic seal and allows liquid drug to flow into the reservoir.

In the third embodiment of the invention, the pleated flexible film reservoir may be provided with an interface comprising a rod disposed along a fluid path used to fill the reservoir with the liquid drug. The rod is connected to a flexible film which seals the fluid port of the reservoir. Pressure from the liquid drug as the reservoir is being filled causes movement of the rod which, in turn, causes the flexible film to be peeled away from the fluid port of the reservoir, thus allowing liquid drug to enter the reservoir.

BRIEF DESCRIPTION OF THE DRAWINGS

FIG. 3A shows the pleats forming the curved side walls of the reservoir as it would appear in an empty state, while FIG. 3B shows the pleats as they would appear when the reservoir is full.

FIG. 5A shows the device in its initial state wherein the flexible strip is covering the fluid port of the reservoir. FIG. 5B shows the device in a second state wherein the flexible strip has been peeled back from the fluid port by the rod.

DETAILED DESCRIPTION

The embodiments of the invention are directed to an expandable, flexible reservoir for a wearable drug delivery device in which the reservoir is composed of a film with high air and water barrier properties, such as a multilayer film with a foil layer. The film defines a top surface, a bottom surface and plurality of pleats between the top and bottom surfaces forming the side walls of the reservoir so as to allow the reservoir to be in a substantially flat configuration when empty and allowing the reservoir to expand as the reservoir is filled with the liquid drug, while avoiding the "pillowing" affect. The pleated design therefore increases the volume and space efficiency of the reservoir.

The novel aspects of the embodiments of the present invention are described in detail below. Several exemplary embodiments are shown herein; however, it should be realized that aspects of the invention are not meant to be limited thereby, but are instead meant to encompass the novel aspects of the various embodiments. The embodiments described herein provide one or more advantages over conventional, prior art systems, components and methods.

Various embodiments of the present invention include systems and methods for delivering a medication to a user using a wearable drug device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be worn or carried on the body of the user and that executes an algorithm that computes the times and dosages of delivery of the medication. For example, the user device may execute an "artificial-pancreas" algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the drug delivery device or may be a separate device. Alternately, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the medical device). In these embodiments, the sensor and/or drug delivery device contain computing hardware (e.g., a processor, memory, firmware, etc.) that executes some or all of the algorithm that computes the times and dosages of delivery of the medication.

Figure 1:
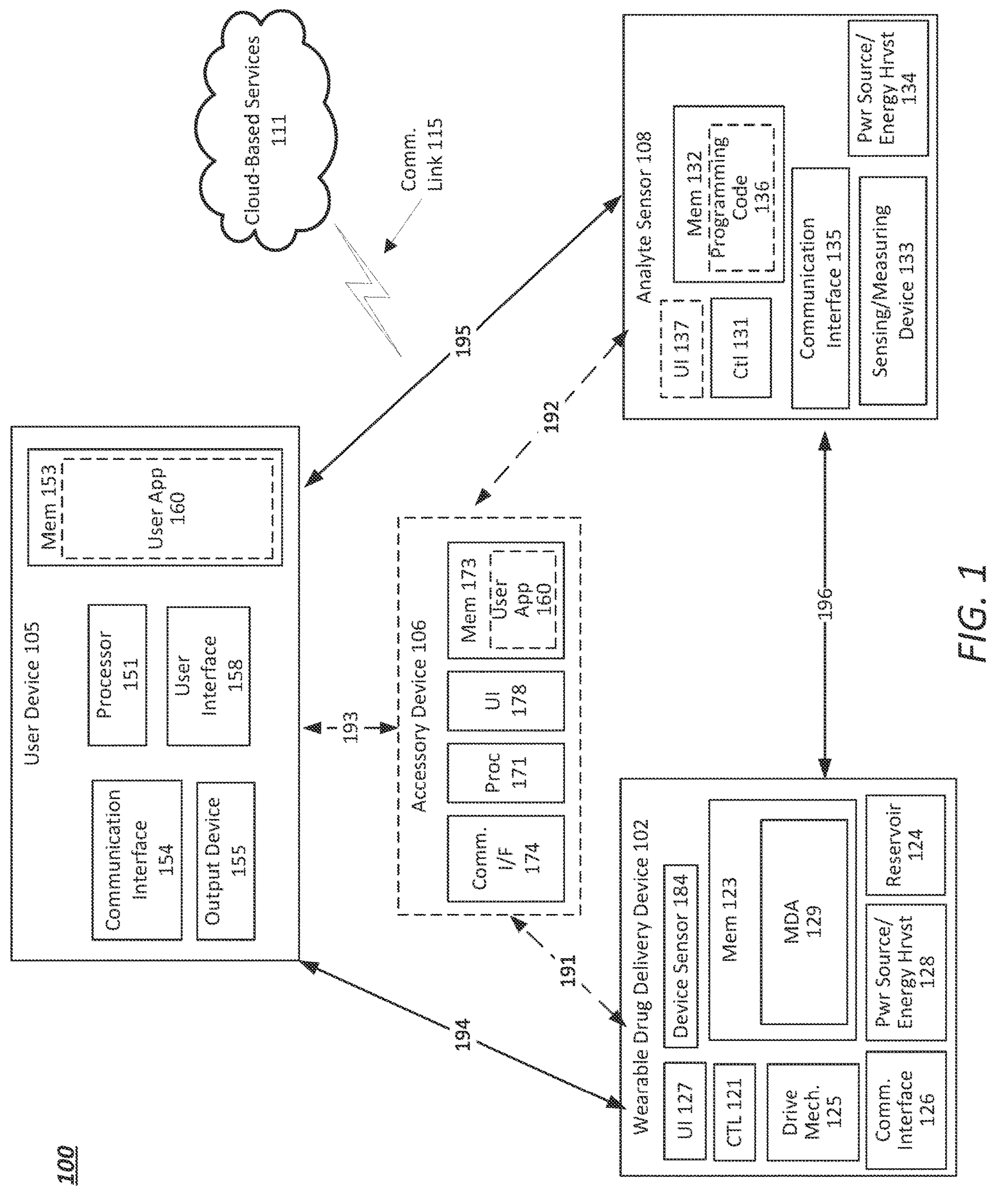
FIG. 1 illustrates a functional block diagram of an exemplary system suitable for implementing the systems and methods disclosed herein.

FIG. 1 illustrates a functional block diagram of an exemplary system suitable for implementing the systems and, methods described herein. The automatic drug delivery system 100 may implement (and/or provide functionality for) a medication delivery algorithm, such as an artificial pancreas (AP) application, to govern or control automated delivery of a drug or medication, such as insulin, to a user (e.g., to maintain euglycemia-a normal level of glucose in the blood). The drug delivery system 100 may be an automated drug delivery system that may include a wearable drug delivery device 102, an analyte sensor 108, and a user device 105.

The system 100, in an optional example, may also include an accessory device 106, such as a smartwatch, a personal assistant device or the like, which may communicate with the other components of system 100 via either a wired or wireless communication links 191-193.

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like as discussed below. The user device 105 may be used to program, adjust settings, and/or control operation of the wearable automatic drug delivery device 102 and/or the analyte sensor 103 as well as the optional smart accessory device 106.

The processor 151 may also be configured to execute programming code stored in device memory 153, such as the user app 160. The user app 160 may be a computer application that is operable to deliver a drug based on information received from the analyte sensor 103, the cloud-based services 111 and/or the user device 105 or optional accessory device 107. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an artificial pancreas (AP) application, the processor 151 is also configured to execute a diabetes treatment plan (which may be stored in a memory) that is managed by user app 160. In addition to the functions mentioned above, when user app 160 is an AP application, it may further provide functionality to determine a carbohydrate-compensation dosage, a correction bolus dosage and determine a basal dosage according to a diabetes treatment plan. In addition, as an AP application, user app 160 provides functionality to output signals to the wearable automatic drug delivery device 102 via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

The wearable automatic drug delivery device 102, in the example system 100, may include a user interface 127, a controller 121, a drive mechanism 125, a communication interface 126, a memory 623, a power source/energy harvesting circuit 128, device sensors 184, and a reservoir 124. The wearable automatic drug delivery device 102 may be configured to perform and execute processes required to deliver doses of the medication to the user without input from the user device 105 or the optional accessory device 106. As explained in more detail, the controller 121 may be operable, for example, to determine an amount of insulin to be delivered, IOB, insulin remaining, and the like, based on an input from the analyte sensor 108.

The memory 123 may store programming code executable by the controller 121. The programming code, for example, may enable the controller 121 to control the delivery of medication from the reservoir 124 and control the administering of doses of medication based on signals from the medication delivery algorithm (MDA) 129 or, external devices, if the MDA 129 is configured to implement the external control signals.

The reservoir 124 may be configured to store drugs, medications or therapeutic agents suitable for automated delivery, such as insulin, GLP-1, co-formulations of insulin and GLP-1, morphine, blood pressure medicines, chemotherapy drugs, fertility drugs or the like.

The device sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between a needle or cannula inserted in a user and the reservoir 124. The pressure sensor may be coupled to or integral with a needle/cannula insertion component (which may be part of the drive mechanism 125) or the like. In an example, the controller 121 or a processor, such as 151, may be operable to determine that a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount.

In an example, the wearable automatic drug delivery device 102 includes a communication interface 126, which may be a transceiver that operates according to one or more radio-frequency protocols, such as Bluetooth, Wi-Fi, near-field communication, cellular, or the like. The controller 121 may, for example, communicate with user device 105 and an analyte sensor 108 via the communication interface 126.

The wearable automatic drug delivery device 102 may be attached to the body of a user, such as a patient or diabetic, at an attachment location and may deliver any therapeutic agent, including any drug or medicine, such as insulin or the like, to a user at or around the attachment location. A surface of the wearable automatic drug delivery device 102 may include an adhesive to facilitate attachment to the skin of a user.

The wearable automatic drug delivery device 102 may, for example, include a reservoir 124 for storing the drug, a needle or cannula (not shown) for delivering the drug into the body of the user (which may be done subcutaneously, intraperitoneally, or intravenously), and a drive mechanism 125 for transferring the drug from the reservoir 124 through a needle or cannula and into the user. The drive mechanism 125 may be fluidly coupled to reservoir 124, and communicatively coupled to the controller 121.

The wearable automatic drug delivery device 102 may further include a power source 128, such as a battery, a piezoelectric device, an energy harvesting devices, or the like, for supplying electrical power to the drive mechanism 125 and/or other components (such as the controller 121, memory 123, and the communication interface 126) of the wearable automatic drug delivery device 102.

In some examples, the wearable automatic drug delivery device 102 and/or the user device 105 may include a user interface 158, and an output device 155, such as a keypad, a touchscreen display, levers, light-emitting diodes, buttons on a housing of the drug delivery device 101, a microphone, a camera, a speaker, a display, or the like, that is configured to allow a user to enter information and allow the user device 105 to output information for presentation to the user (e.g., alarm signals or the like). The user interface 158 may provide inputs, such as a voice input, a gesture (e.g., hand or facial) input to a camera, swipes to a touchscreen, or the like, to processor 151 which the user app 160 interprets.

When configured to communicate with an external device, such as the user device 105 or the analyte sensor 108, the wearable automatic drug delivery device 102 may receive signals over the wired or wireless link 194 from the user device 105 or from the analyte sensor 108. The controller 121 of the wearable automatic drug delivery device 102 may receive and process the signals from the respective external devices as well as implementing delivery of a drug to the user according to a diabetes treatment plan or other drug delivery regimen.

In an operational example, the processor 121, when executing user app 160, may output a control signal operable to actuate the drive mechanism 125 to deliver a carbohydrate-compensation dosage of insulin, a correction bolus, a revised basal dosage or the like.

The accessory device 107 may be, for example, an Apple Watch®, other wearable smart device, including eyeglasses, smart jewelry, a global positioning system-enabled wearable, a wearable fitness device, smart clothing, or the like. Similar to user device 105, the accessory device 107 may also be configured to perform various functions including controlling the wearable automatic drug delivery device 102. For example, the accessory device 107 may include a communication interface 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the user app 160, or a pared-down versions of user app 160 with reduced functionality.

The analyte sensor 108 may include a controller 131, a memory 132, a sensing/measuring device 133, an optional user interface 137, a power source/energy harvesting circuitry 134, and a communication interface 135. The analyte sensor 603 may be communicatively coupled to the processor 651 of the management device 605 or controller 621 of the wearable automatic drug delivery device 602. The memory 632 may be configured to store information and programming code 136.

The analyte sensor 108 may be configured to detect multiple different analytes, such as lactate, ketones, uric acid, sodium, potassium, alcohol levels or the like, and output results of the detections, such as measurement values or the like. The analyte sensor 108 may, in an exemplar embodiment, be configured to measure a blood glucose value at a predetermined time interval, such as every 5 minutes, or the like. The communication interface 135 of analyte sensor 108 may have circuitry that operates as a transceiver for communicating the measured blood glucose values to the user device 105 over a wireless link 195 or with wearable automatic drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 121 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from the wearable automatic drug delivery device 102, in various examples, the analyte sensor 108 and wearable automatic drug delivery device 102 may be incorporated into the same unit. That is, in various examples, the analyte sensor 108 may be a part of and integral with the wearable automatic drug delivery device 102 and contained within the same housing as the wearable automatic drug delivery device 102. In such an example configuration, the controller 121 may be able to implement the functions required for the proper delivery of the medication alone without any external inputs from user device 105, the cloud-based services 111, another sensor (not shown), the optional accessory device 107, or the like.

The communication link 115 that couples the cloud-based services 111 to the respective devices 102, 105, 106, 108 of system 100 may be a cellular link, a Wi-Fi link, a Bluetooth link, or a combination thereof. Services provided by cloud-based services 111 may include data storage that stores anonymized data, such as blood glucose measurement values, historical IOB or TDI, prior carbohydrate-compensation dosage, and other forms of data. In addition, the cloud-based services 111 may process the anonymized data from multiple users to provide generalized information related to TDI, insulin sensitivity, IOB and the like.

The wireless communication links 191-196 may be any type of wireless link operating using known wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 154, 174, 126 and 135.

The user app 160 (or MDA 129) may provide periodic insulin micro-boluses based upon the predicted glucose over a 60-minute prediction horizon. Optimal post-prandial control will require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

The user application 160 implements a graphical user interface that is the primary interface with the user and is used to start and stop a wearable drug delivery device 102, program basal and bolus calculator settings for manual mode as well as program settings specific for automated mode (hybrid closed-loop or closed-loop).

In manual mode, user app 160 will deliver insulin at programmed basal rates and bolus amounts with the option to set temporary basal profiles. The controller 121 will also have the ability to function as a sensor-augmented pump in manual mode, using sensor glucose data provided by the analyte sensor 108 to populate the bolus calculator.

In automated mode, the user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

User app 160, allows the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

In some embodiments, user device 105 and the analyte sensor 108 may not communicate directly with one another. Instead, data (e.g., blood glucose readings) from analyte sensor may be communicated to drug delivery device 102 via link 196 and the relayed top user device 102 via link 194. In some embodiments, to enable communication between analyte sensor 108 and user device 102, the serial number of the analyte sensor must be entered into user app 160.

User ap 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (IOB). IOB is estimated by user app 160 taking into account any manual bolus and insulin delivered by the algorithm.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

The primary embodiments of the invention are directed to a reservoir suitable for use in a pump mechanism of a wearable drug delivery device, such as the one described with reference to FIG. 1.

Figures 2A, 2B, 2C:
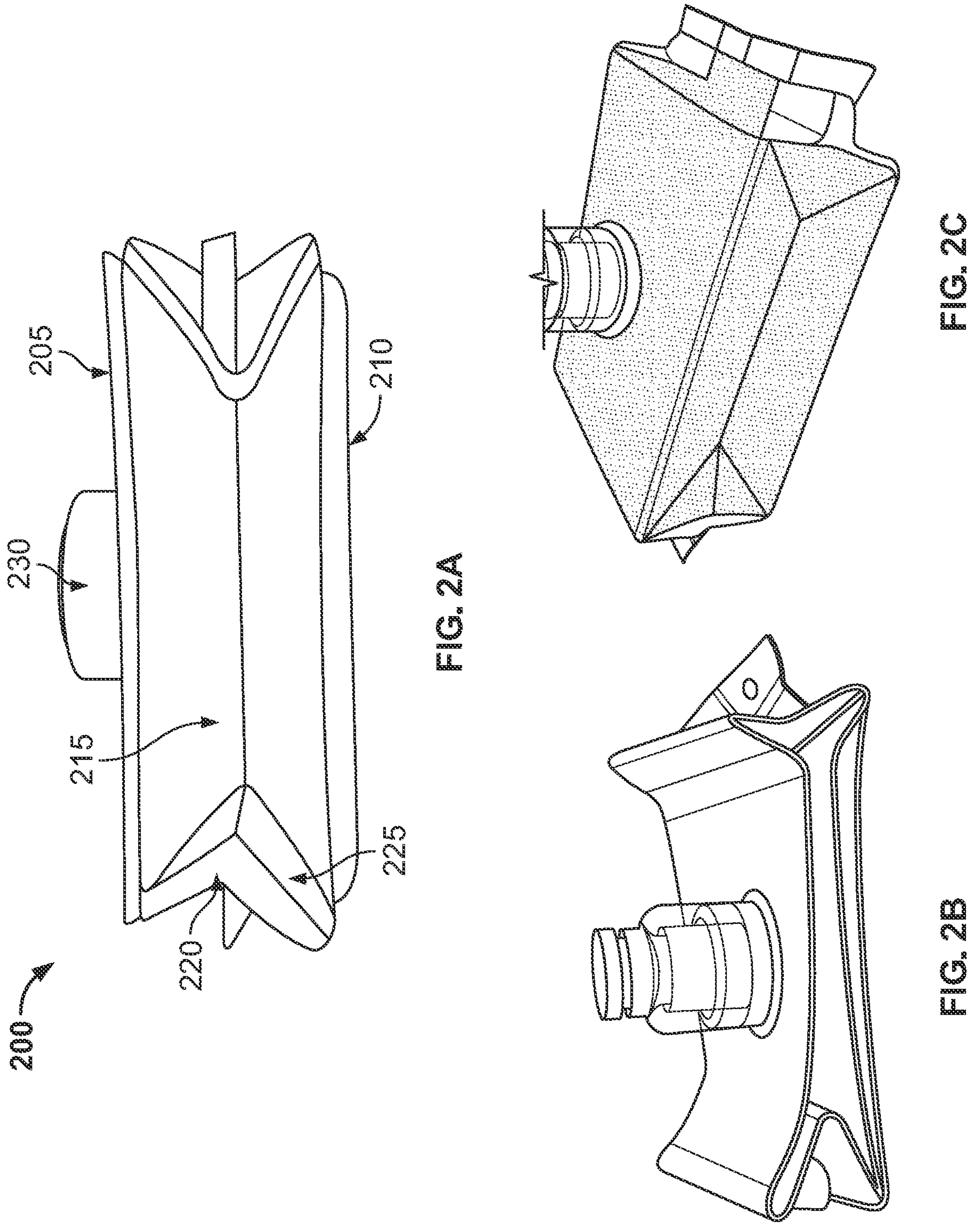
FIG. 2A is a side view of an exemplary rectangular-shaped reservoir having pleated sides in accordance with a first embodiment of the invention.
FIGS. 2B and 2C show the reservoir of FIG. 2A in an empty state and in a filled state, respectively.

FIG. 2A shows an exemplary implementation of a first embodiment of the invention, showing the reservoir 200 as a four-sided rectangular structure. As shown in FIG. 2A in a side view of the embodiment, reservoir 200 is provided with pleats 215 on the longer side and pleats 220 on the shorter side between a top surface 205 and a bottom surface 210. Each of pleats 215, 220 may be formed by folding the film material, of which reservoir 200 is constructed, between top surface 205 and bottom surface 210 in a first direction parallel to the top surface 205 and bottom surface 210. The folding of a pleat in the first direction will cause a fold in adjacent pleats in a second direction to form a connecting portion 225 between adjacent pleats.

The pleats 215, 220 may be formed by any known methods of shaping the film material from which reservoir 200 is constructed. For example, the pleats 215, 220 may be made by folding the film material and applying a heat seal to form the folds in the desired configuration to form the pleats 215, 220. Alternatively, pleats 215, 220 may be formed independently and heat sealed to each other or to the top surface 205 and bottom surface 210 of reservoir 200.

In a variation of this embodiment, not shown, the pleats 210, 215 may be stacked in multiple rows between the top surface 205 and the bottom surface 210, so as to provide greater expandability of reservoir 200.

Note that fluid port 230 is shown as being located on a top surface 205 of reservoir 200. This is exemplary only and the invention is not meant to be limited thereby. Fluid port 230 may be disposed on any surface of reservoir 200 of the embodiments disclosed herein.

FIG. 2B shows reservoir 200 in its empty state wherein the pleats 215, 220 forming the sides of reservoir 200 are folded in a substantially flat configuration. The pleats are designed so that as the air is evacuated from reservoir 200 during the manufacturing process, the vacuum created within reservoir 200 will cause folding of the pleats 215, 220 and flattening of reservoir 200 to a minimal size. Note that the reservoir 200, as shown in FIG. 2B, has not been evacuated of air to form a vacuum therein, but is expanded slightly to show the pleats formed therein.

FIG. 2C shows reservoir 200 in the state wherein it is filled with a liquid drug. The introduction of the liquid drug into reservoir 200 causes expansion of the pleats 215, 220 to create space within reservoir 200, while also avoiding the pillowing effect. The pillowing effect would occur if the reservoir was provided without pleats 215, 220, for example, in an embodiment wherein the top surface 205 and the bottom surface 210 of reservoir 200 are heat sealed to each other at their edges (or sealed to non-pleated side walls) such that the introduction of the liquid drug into the reservoir would cause the top and bottom to expand to a rounded form while still touching at the edges. The pleated design avoids this space-inefficient result.

Figure 3A:
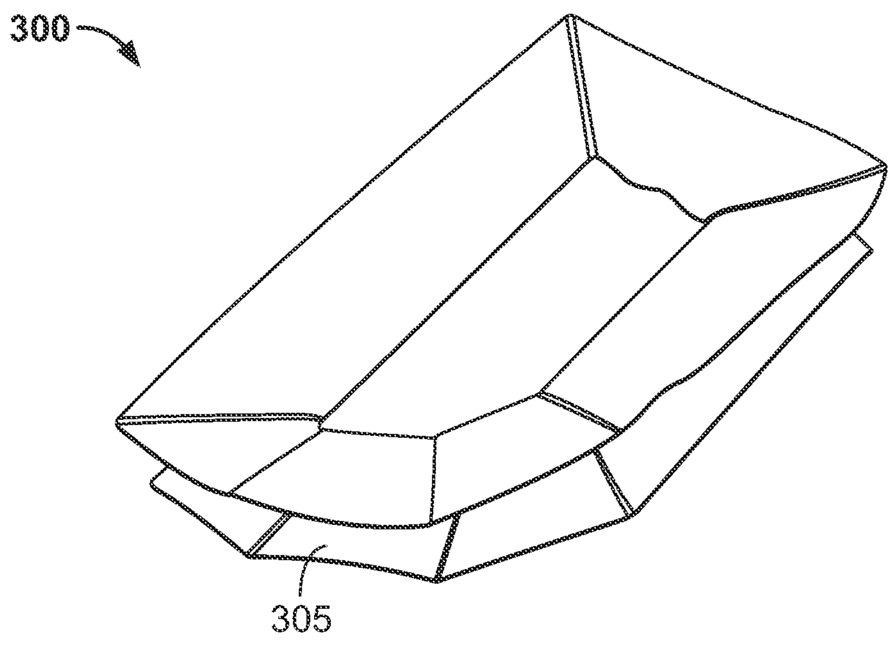
FIGS. 3A and 3B show a second aspect of the embodiment of the reservoir of FIG. 2A showing a mockup of a reservoir (with the top and bottom removed) having curved side walls designed to fit the interior contour of the wearable drug delivery.
Figure 3B:
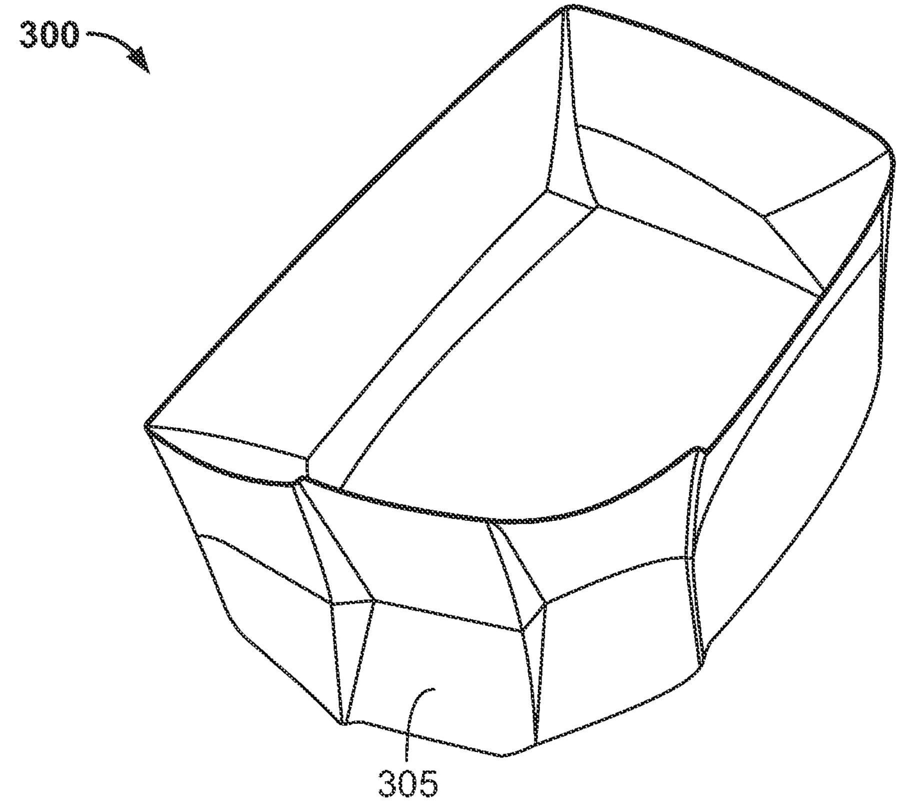

FIGS. 3A, 3B show a variation of the first embodiment of the invention wherein the reservoir 300 is of an irregular shape. The irregular shape, when fitted into a wearable drug delivery device having one or more housings forming an interior contour, will more efficiently utilize the space within the interior of the housings. In this embodiment, pleats 305 form non-right angles with respect to each other to create the curved side walls shown in the figures. In variations of the first embodiment, the number and size of the pleats 305 may be varied to form reservoir 300 in any desired shape. In such cases, the top and bottom surfaces of reservoir 300 can be shaped to match the curvature of the side walls.

FIG. 3A shows a first state wherein the pleats 305 are compressed, thereby flattening reservoir 300. For illustration purposes, reservoir 305 is shown without the top and bottom surfaces in these figures. FIG. 3B shows a second state wherein the pleats 305 are expanded, showing the manner in which the pleats 305 form the curved portions of reservoir 300.

Figure 4:
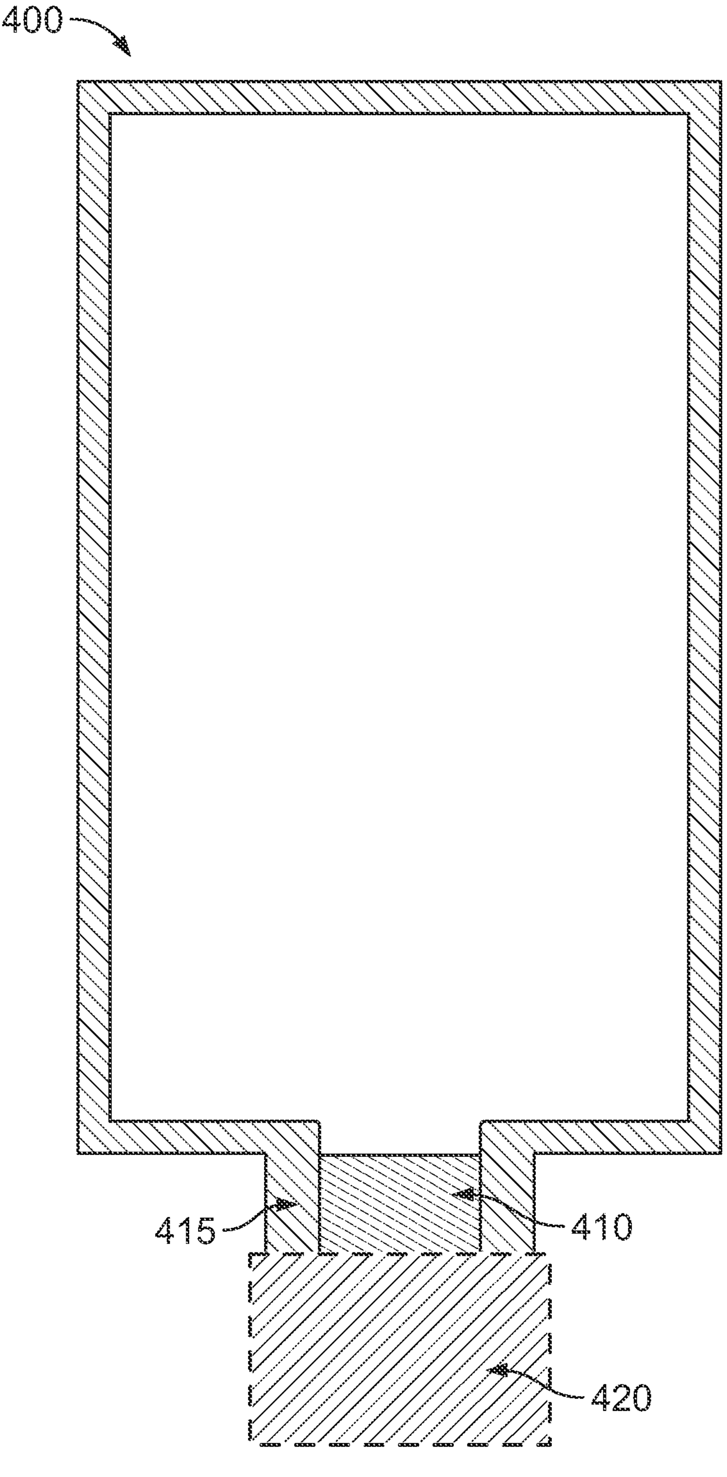
FIG. 4 is a top view of a reservoir in accordance with the third embodiment of the invention having a hermetic seal between a fluid port and the interior of the reservoir.

FIG. 4 shows a top view of a second embodiment of the invention. As stated in the Summary section herein, when the reservoir is vacuum sealed, it may be difficult to make a fluid port that can maintain the vacuum inside the reservoir for the duration of the shelf life of the device.

In this embodiment, reservoir 400, may be any one of the reservoir implementations previously described herein or may be any other embodiment of a flexible reservoir (e.g., reservoir 200 or 300). In this embodiment, fluid port 415 of reservoir 400 is provided with a hermetic seal 410 to aid in the maintenance of the vacuum inside reservoir 405. Hermetic seal 410 may be designed to be mechanically weak, such that, as pressurized liquid drug is forced into fluid port 415 via fluid path 420, the pressure is strong enough to break the mechanically weak hermetic seal 410, thereby allowing fluid communication between fluid path 420 and the interior of reservoir 400.

Figure 5A:
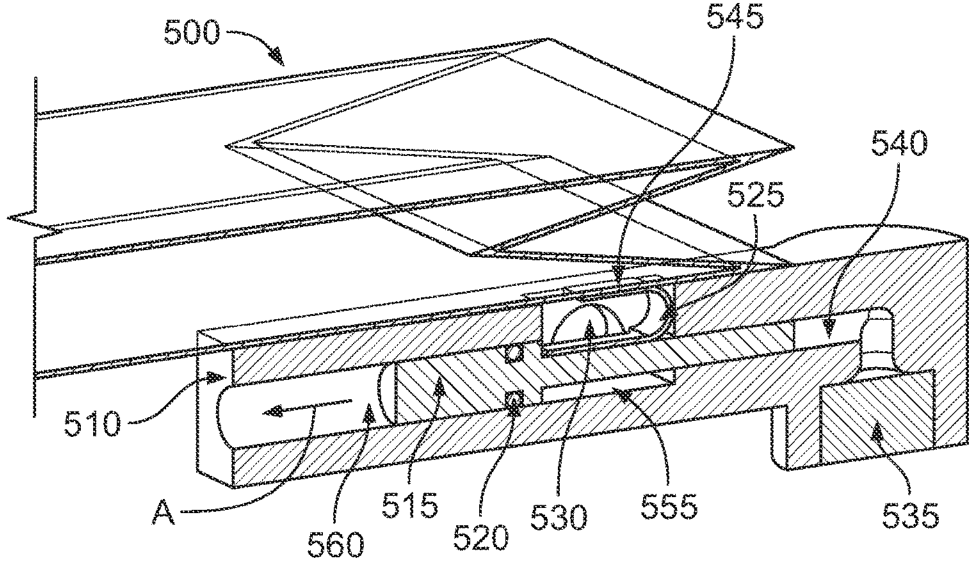
FIGS. 5A and 5B show isometric, cross-sectional views of a fourth embodiment of the invention wherein the pleated reservoir is fitted with a structure containing the fluid path for introducing the liquid drug into the reservoir and in which a rod disposed in the fluid path is attached to a flexible strip which seals a fluid port of the reservoir.
Figure 5B:
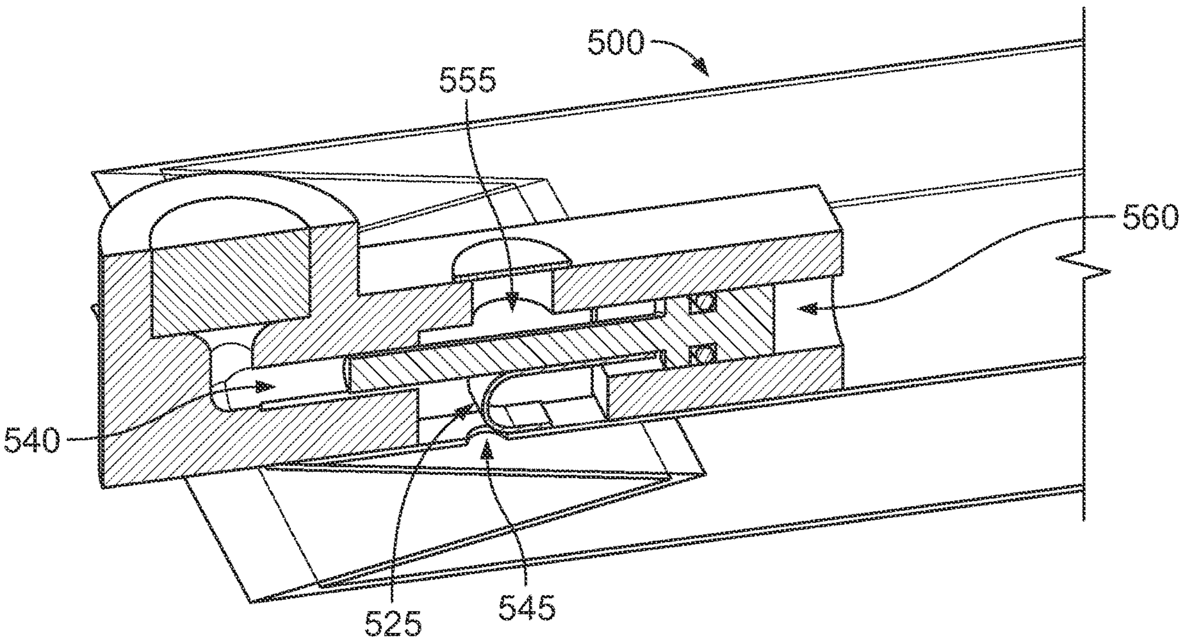

FIGS. 5A, 5B show isometric, cross-sectional views of a third embodiment of the invention. This embodiment of the invention is also designed to maintain the vacuum within the interior of the reservoir during the shelf life of the wearable drug delivery device. The reservoir 500 in the third embodiment may be any one of the reservoirs previously described herein (e.g., reservoir 200, 300, or 400) or may be any other embodiment of a flexible reservoir.

In this embodiment, reservoir 500 is fitted with a structure 510 which defines a fluid path 540 therein for filling the reservoir 500. Fluid path 540 may be sealed by septum 535. During the filling process, the user inserts a needle through septum 535 and injects the liquid drug into fluid path 540. As the liquid drug flows into fluid path 540, it forces rod 515 to linearly translate in direction "A". When rod 515 clears the wall between and fluid path 540 and area 555, enabling fluid communication between fluid path 540 and area 555, rod 515 will cease movement in direction "A" until any air within area 555 is evacuated through air port 530 by the pressure caused by the liquid drug entering area 555. Preferably, air port 530 is composed of a hydrophobic material that will allow air to escape while confining the liquid drug within area 555.

Rod 515 may be fitted with one or more O-rings 520 to create a friction seal within area 560. Preferably, the friction seal is strong enough to prevent plunger 515 from translating in direction "A" until all of the air has been evacuated from area 555. Thereafter, the pressure of the liquid drug entering area 555 will cause rod 515 to continue to translate in direction "A" within area 560.

Fluid port 545 of reservoir 500 is sealed with a flexible strip 525. In preferred embodiments of the invention, flexible strip 525 may be fitted with an adhesive or a week mechanical link which bonds it to reservoir 500 so as to seal fluid port 545, as shown in FIG. 5A. Flexible strip 525 is also mechanically coupled to rod 515. As rod 515 is forced by the pressure of the liquid drug entering area 555 to translate in direction "A" through area 560, the motion causes flexible strip 525 to tear away from fluid port 545 of reservoir 500, thereby opening fluid port 545. This places reservoir 500 in fluid communication with fluid path 540, and allows the liquid drug to enter reservoir 500, as shown in FIG. 5B. Preferably, the dimensions of fluid path 540, area 555, and area 560 will be minimized to reduce the holdup volume of the liquid drug.

The following examples pertain to various embodiments of the invention:

Example 1 is a reservoir having a top surface, a bottom surface and a plurality of pleats forming side walls connecting the top and bottom surfaces when the reservoir is composed of film having high air and water vapor barrier properties.

Example 2 is an extension of Example 1, or any other example disclosed herein, wherein the side walls comprise a single row of pleats between the top and bottom surfaces.

Example 3 is an extension of Example 1, or any other example disclosed herein, wherein the side walls comprise multiple rows of pleats between the top and bottom surfaces.

Example 4 is an extension of Example 1, or any other example disclosed herein, wherein some of the pleats forming the side walls of the reservoir are arranged at non-right angles with respect to each other to form curved side walls.

Example 5 is an extension of Example 1, or any other example disclosed herein, wherein the pleats are formed by folding the material in a first direction parallel to the top and bottom surfaces.

Example 6 is an extension of Example 5, or any other example disclosed herein, wherein the folding of the pleat in a direction parallel to the top and bottom surfaces cause a folding of adjacent pleats in a second direction to form a connecting portion between the adjacent pleats.

Example 7 is an extension of Example 1, or any other example disclosed herein, wherein the reservoir further comprises a fluid port to enable fluid communication with the reservoir.

Example 8 is a reservoir comprising an enclosure formed of a film having a fluid port defined therein and a mechanically weak hermetic seal sealing the fluid port.

Example 9 is an extension of Example 8, or any other example disclosed herein, wherein the enclosure comprises a top surface, a bottom surface and a plurality of pleats forming side walls connecting the top and bottom surfaces.

Example 10 is an extension of Example 9, or any other example disclosed herein, wherein at least some of the plurality of pleats are arranged in non-right angles with respect to each other to form curved side walls.

Example 11 is a reservoir comprising an enclosure, a fluid port defined in the enclosure, a fluid path coupled to the fluid port, a foil strip sealing the fluid port and a rod, disposed in the fluid path and coupled to the foil strip.

Example 12 is an extension of Example 11, or any other example disclosed herein, wherein a pressure introduced into the fluid path causes the rod to translate within the fluid path thereby tearing the foil strip away from the fluid port.

Example 13 is an extension of Example 11, or any other example disclosed herein, wherein the enclosure comprises a top surface, a bottom surface and a plurality of pleats forming side walls connecting the top and bottom surfaces.

Example 14 is an extension of Example 11, or any other example disclosed herein, further comprising a septum sealing the fluid path.

Example 15 is extension of Example 11, or any other example disclosed herein, further comprising an air port defined in the fluid path.

Example 16 is an extension of Example 15, or any other example disclosed herein, wherein the air port is composed of a hydrophobic material.

Certain embodiments of the present invention were described above. It is, however, expressly noted that the present invention is not limited to those embodiments, but rather it is intended that additions and modifications to the expressly described embodiments herein are also to be included within the scope of the invention. Moreover, it is to be understood that the features of the various embodiments described herein are not mutually exclusive and can exist in various combinations and permutations, even if such combinations or permutations were not made express herein, without departing from the spirit and scope of the invention. As such, the invention is not to be defined only by the preceding illustrative description. Future filed applications claiming priority to this application may claim the disclosed subject matter in a different manner and may generally include any set of one or more limitations as variously disclosed or otherwise demonstrated herein.

The invention claimed is:

1. A reservoir comprising:

a top surface;

a bottom surface; and a plurality of pleats forming one or more side walls connecting the top surface and the bottom surface;

wherein the top surface, the bottom surface and the plurality of pleats are composed of a film having high air and water vapor barrier properties.

2. The reservoir of claim 1 wherein the one or more side walls comprise a single row of pleats between the top and bottom surfaces.

3. The reservoir of claim 1 wherein the one or more side walls comprise a plurality of rows of pleats between the top and bottom surfaces.

4. The reservoir of claim 1 wherein at least some of the plurality of pleats are arranged at non-right angles with respect to adjacent pleats so as to form curved side walls between the top and bottom surfaces.

5. The reservoir of claim 1 wherein the plurality of pleats are formed by folding the film material between the top and bottom surfaces in a first direction parallel to the top and bottom surfaces.

6. The reservoir of claim 5 wherein the folding of a pleat in the first direction will cause a fold in adjacent pleats in a second direction to form a connecting portion between adjacent pleats.

7. The reservoir of claim 1 further comprising a fluid port enabling fluid communication with the reservoir.

8. The reservoir of claim 1, wherein the reservoir comprises a flexible enclosure formed of plastic film, and the plurality of pleats are formed in the film between the top and bottom surfaces to avoid a pillowing effect when filled.

9. The reservoir of claim 1, wherein the pleats are arranged at non-right angles with respect to each other to fit interior contours of a wearable device housing.

10. A reservoir comprising:

an enclosure formed of a film having high air and water vapor barrier properties;

a fluid port, defined in the enclosure; and a hermetic seal sealing the fluid port;

wherein the hermetic seal is mechanically weak such that a pressure applied to the hermetic seal via a fluid path coupled to the fluid port will cause the hermetic seal to break to enable fluid communication between the fluid path and the enclosure.

11. The reservoir of claim 10 wherein the enclosure comprises:

a top surface;

a bottom surface; and a plurality of pleats forming one or more side walls connecting the top surface and the bottom surface.

12. The reservoir of claim 11 wherein at least some of the plurality of pleats are arranged at non-right angles with respect to adjacent pleats such as to form curved side walls between the top and bottom surfaces.

13. A reservoir comprising:

an enclosure formed of a film having high air and water vapor barrier properties;

a fluid port, defined in the enclosure;

a fluid path, coupled to the fluid port;

a foil strip bonded to the enclosure such as to seal the fluid port; and a rod, coupled to the foil strip and disposed in the fluid path.

14. The reservoir of claim 13 wherein a pressure introduced into the fluid path causes the rod to translate within the fluid path and further wherein the translation of the rod causes the foil strip to tear away from the fluid port, thereby enabling fluid communication between the fluid path and the enclosure.

15. The reservoir of claim 13 wherein the enclosure comprises:

a top surface;

a bottom surface; and a plurality of pleats forming one or more side walls connecting the top surface and the bottom surface.

16. The reservoir of claim 13 further comprising:

a septum, sealing the fluid path;

wherein the pressure is introduced into the fluid path by a fluid from a needle pushed through the septum.

17. The reservoir of claim 13 further comprising:

an air port, defined in the fluid path, to allow air to escape the fluid path when a fluid is introduced into the fluid path.

18. The reservoir of claim 17 wherein the air port is composed of hydrophobic material that allows the passage of air but prevents the passage of the fluid.

* * * * *